(12) United States Patent
Okamoto et al.

(10) Patent No.: US 11,141,056 B2
(45) Date of Patent: Oct. 12, 2021

(54) OPHTHALMIC DEVICE

(71) Applicant: Tomey Corporation, Nagoya (JP)

(72) Inventors: Keiichiro Okamoto, Nagoya (JP); Risa Higashita, Nagoya (JP); Chuang Hsin Yuan, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 59 days.

(21) Appl. No.: 16/427,709

(22) Filed: May 31, 2019

(65) Prior Publication Data
US 2019/0365218 A1 Dec. 5, 2019

(30) Foreign Application Priority Data
Jun. 4, 2018 (JP) .............................. JP2018-107209

(51) Int. Cl.
*A61B 3/00* (2006.01)
*A61B 3/14* (2006.01)
*A61B 3/10* (2006.01)

(52) U.S. Cl.
CPC ............ *A61B 3/0025* (2013.01); *A61B 3/102* (2013.01); *A61B 3/14* (2013.01)

(58) Field of Classification Search
CPC .......... A61B 3/0025; A61B 3/102; A61B 3/14
USPC ......... 351/200, 205–206, 209–211, 221–223
See application file for complete search history.

(56) References Cited

U.S. PATENT DOCUMENTS

| | | | |
|---|---|---|---|
| 2002/0186875 A1* | 12/2002 | Burmer ................... | G06K 9/66 382/133 |
| 2012/0083667 A1 | 4/2012 | Isogai et al. | |
| 2012/0121158 A1 | 5/2012 | Sekine et al. | |
| 2012/0127428 A1* | 5/2012 | Isogai .................... | A61B 3/102 351/206 |
| 2014/0078466 A1 | 3/2014 | Sekine et al. | |
| 2014/0167762 A1* | 6/2014 | Sugiyama .......... | G01R 33/3858 324/322 |
| 2016/0360962 A1* | 12/2016 | Okamoto ............... | A61B 3/117 |

FOREIGN PATENT DOCUMENTS

| | | |
|---|---|---|
| JP | 2011-024930 A | 2/2011 |
| JP | 2017-093854 A | 6/2017 |
| JP | 2018-051071 A | 4/2018 |

* cited by examiner

*Primary Examiner* — Brandi N Thomas
(74) *Attorney, Agent, or Firm* — Shumaker, Loop & Kendrick, LLP

(57) ABSTRACT

An ophthalmic device that includes an image capturing unit configured to capture a tomographic image of a crystalline lens of a subject eye; a processor; and a memory storing computer-readable instructions therein. The computer-readable instructions, when executed by the processor, may cause the processor to execute: detecting a boundary between tissues in a tomographic image of the crystalline lens of the subject eye captured by the image capturing unit; determining whether the tissues defined by the boundary include an abnormality; and analyzing an analysis item associated with the abnormality.

4 Claims, 10 Drawing Sheets

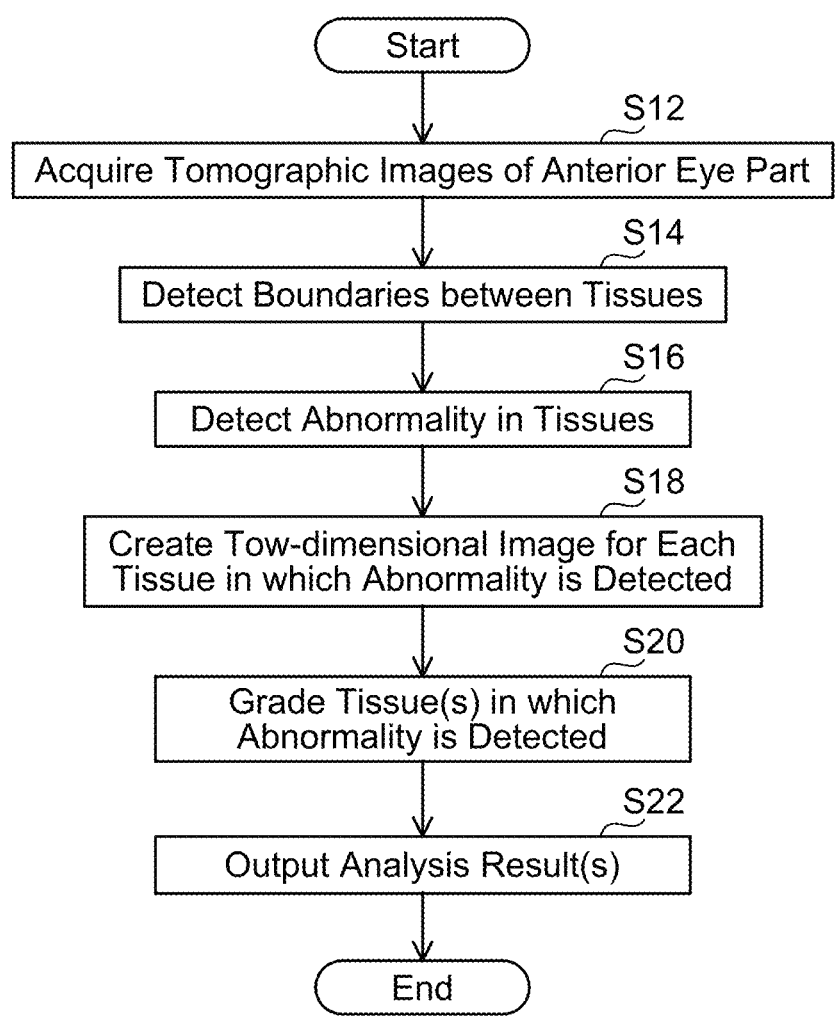

ized*

OPHTHALMIC DEVICE

CROSS-REFERENCE

This application claims priority to Japanese Patent Application No. 2018-107209, filed on Jun. 4, 2018, the entire contents of which are incorporated herein by reference.

TECHNICAL FIELD

The technique disclosed herein relates to an ophthalmic device. To be more precise, it relates to an ophthalmic device configured to capture a tomographic image of a crystalline lens of a subject eye.

BACKGROUND ART

To investigate a condition of a crystalline lens of a subject eye, observation of the crystalline lens is performed. An observation method using a slit lamp microscope is generally known for the observation of crystalline lens. For example, as described in Japanese Patent Application Publication No. 2018-051071, in this method, an examiner such as a doctor directly observes the condition of a crystalline lens by irradiating the subject eye with a slit lamp.

SUMMARY

In the observation using the slit lamp microscope of Japanese Patent Application Publication No. 2018-051071, the examiner directly observes the subject eye and diagnoses the condition of the crystalline lens of the subject eye. However, since the examiner adjusts a position irradiated with light from the slit lamp, irradiating a same position with the slit lamp is difficult, thus there has been a problem that variations in diagnosis results occur depending on examinations. The disclosure herein discloses a technique for accurately analyzing a crystalline lens of a subject eye.

An ophthalmic device disclosed herein may comprise: an image capturing unit configured to capture a tomographic image of a crystalline lens of a subject eye; a processor; and a memory storing computer-readable instructions therein. The computer-readable instructions, when executed by the processor, may cause the processor to execute: detecting a boundary between tissues in a tomographic image of the crystalline lens of the subject eye captured by the image capturing unit; determining whether the tissues defined by the boundary include an abnormality; and analyzing an analysis item associated with the abnormality.

BRIEF DESCRIPTION OF DRAWINGS

FIG. 4 is a flowchart showing an example of a process of analyzing a crystalline lens of a subject eye.

FIG. 8A shows a tomographic image of the crystalline lens and FIG. 8B shows the En-face image of the front cortex.

DETAILED DESCRIPTION

Figure 1:
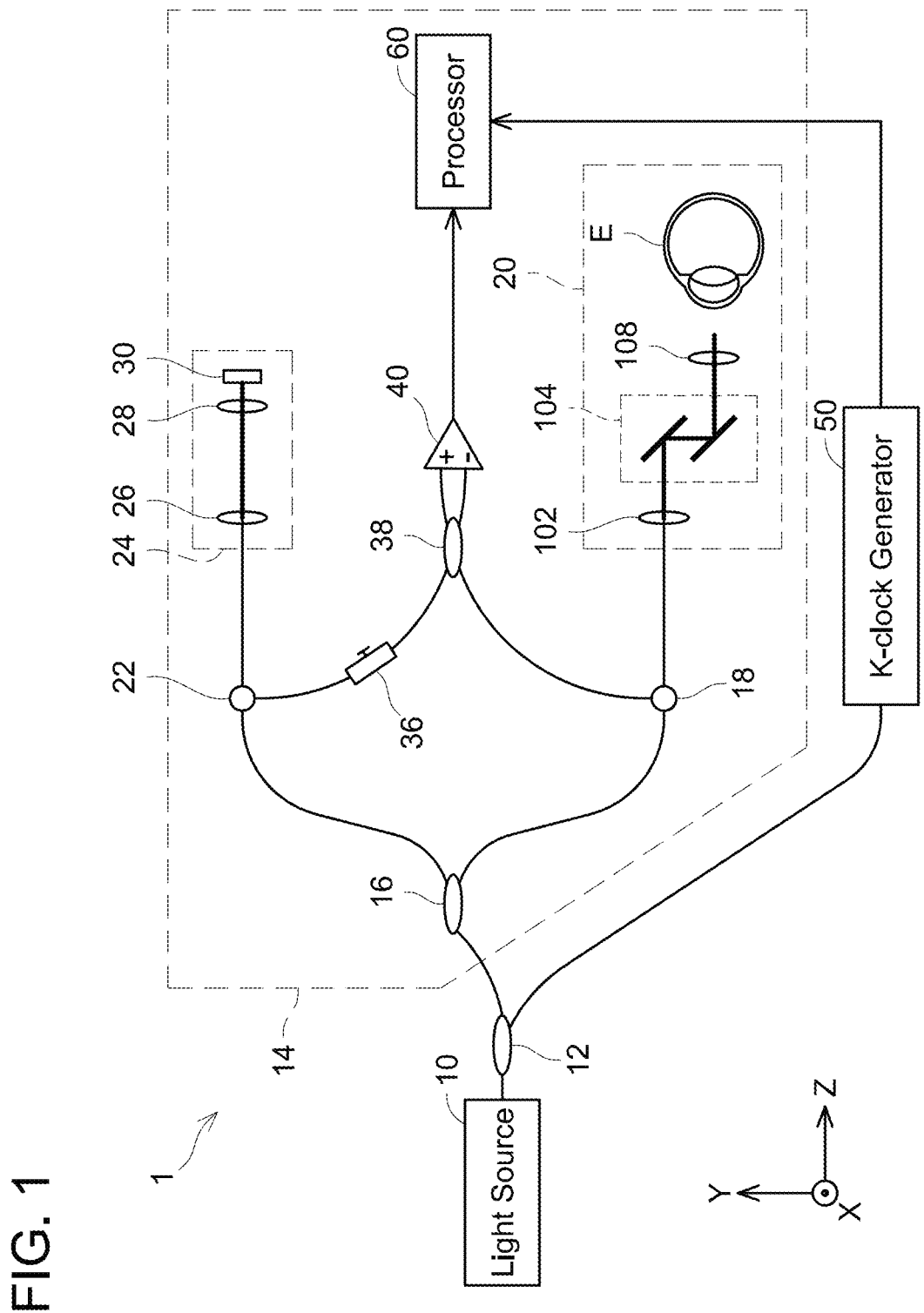
FIG. 1 shows a schematic configuration of an optical system of an ophthalmic device according to an embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic devices, as well as methods for using and manufacturing the same.

Moreover, combinations of features and steps disclosed in the following detailed description may not be necessary to practice the present disclosure in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

An ophthalmic device disclosed herein may comprise: an image capturing unit configured to capture a tomographic image of a crystalline lens of a subject eye; a processor; and a memory storing computer-readable instructions therein. The computer-readable instructions, when executed by the processor, may cause the processor to execute: detecting a boundary between tissues in a tomographic image of the crystalline lens of the subject eye captured by the image capturing unit; determining whether the tissues defined by the boundary include an abnormality; and analyzing an analysis item associated with the abnormality.

The above ophthalmic device analyzes the crystalline lens by using the tomographic image of the crystalline lens of the subject eye captured by the image capturing unit. Due to this, by positioning the image capturing unit relative to the subject eye, image capture and analysis can be executed for a same portion in the crystalline lens, by which variations in diagnosis results among examinations can be avoided. Further, detecting the boundary between tissues enables analysis for each of the tissues. Further, by analyzing the analysis item associated with the detected abnormality, an analysis for an analysis item that is not associated with the detected abnormality can be eliminated, by which processing speed required for the analysis can be increased. Due to this, diagnosis time can be shortened, and burden on a subject can be reduced.

The ophthalmic device disclosed herein may further comprise a display unit configured to display an analysis result. When the abnormality is detected, the display unit may be configured to display an analysis result of the analysis item. According to such a configuration, the analysis result for the analysis item associated with the detected abnormality is displayed on the display unit, by which details of the detected abnormality can be notified to an examiner.

In the ophthalmic device disclosed herein, when the abnormality is detected in a nucleus of the crystalline lens, the display unit may be configured to display the tomographic image of the crystalline lens captured by the image capturing unit by coloring the nucleus of the crystalline lens in a plurality of different colors based on luminance in the tomographic image of the crystalline lens. Such a configuration allows the examiner to easily recognize a condition of the nucleus if the abnormality is detected in the nucleus of the crystalline lens.

EMBODIMENT

Hereinbelow, an ophthalmic device 1 according to an embodiment will be described. The ophthalmic device 1 is configured to capture tomographic images of an anterior eye part of a subject eye E by using an Optical Coherence Tomography (OCT). As shown in FIG. 1, the ophthalmic device 1 includes a light source 10, an interference optical system 14 configured to cause reflected light reflected from the subject eye E and reference light to interfere with each other, and a K-clock generator 50 configured to generate K-clock signals.

The light source 10 is a wavelength-sweeping light source, and is configured to change a waveform of the light emitted therefrom in a predetermined cycle. When the wavelength of the light emitted from the light source 10 changes, a reflected position of reflected light that interferes with the reference light, among reflected light from respective parts of the subject eye E in a depth direction, changes in the depth direction of the subject eye E in accordance with the wavelength of the emitted light. Due to this, it is possible to specify positions of the respective parts (such as a cornea and a crystalline lens) inside the subject eye E by measuring the interference light while changing the wavelength of the emitted light.

The light outputted from the light source 10 is inputted to a fiber coupler 12 through an optical fiber. The light inputted to the fiber coupler 12 is split in the fiber coupler 12, and the split light is outputted to a fiber coupler 16 and the K-clock generator 50 through optical fibers. The K-clock generator 50 will be described later.

The interference optical system 14 includes a measurement optical system configured to irradiate inside of the subject eye E with light from the light source 10 and generate reflected light therefrom, a reference optical system configured to generate reference light from the light of the light source 10, and a balance detector 40 configured to detect interference light that is a combination of the reflected light guided by the measurement optical system and the reference light guided by the reference optical system.

The measurement optical system is constituted of the fiber coupler 16, a circulator 18, and a scanning-alignment optical system 20. The light outputted from the light source 10 and inputted to the fiber coupler 16 through the fiber coupler 12 is split in the fiber coupler 16 into measurement light and reference light, and these light are outputted therefrom. The measurement light outputted from the fiber coupler 16 is inputted to the circulator 18 through an optical fiber. The measurement light inputted to the circulator 18 is outputted to the scanning-alignment optical system 20. The scanning-alignment optical system 20 is configured to irradiate the subject eye E with the measurement light outputted from the circulator 18 and to output reflected light from the subject eye E to the circulator 18. The reflected light inputted to the circulator 18 is inputted to one of inputs of a fiber coupler 38. The scanning-alignment optical system 20 will be described later in detail.

The reference optical system is constituted of the fiber coupler 16, a circulator 22, and a reference unit 24. The reference light outputted from the fiber coupler 16 is inputted to the circulator 22 through an optical fiber. The reference light inputted to the circulator 22 is outputted to the reference unit 24. The reference unit 24 is constituted of collimator lenses 26, 28 and a reference mirror 30. The reference light outputted to the reference unit 24 is reflected by the reference mirror 30 through the collimator lenses 26, 28, and is outputted from the reference unit 24 through the collimator lenses 26, 28 again. The reference light outputted from the reference unit 24 is outputted to the circulator 22. The collimator lens 28 and the reference mirror 30 are each configured to be moved forward and rearward relative to the collimator lens 26 by a second driver 54 (see FIG. 3). When the second driver 54 moves the collimator lens 28 and the reference mirror 30, an optical path length of the reference optical system changes. Due to this, the optical path length of the reference optical system can be adjusted to be substantially equal to an optical path length of the measurement optical system. The reference light inputted to the circulator 22 is inputted to another input of the fiber coupler 38 through a polarized wave controller 36. The polarized wave controller 36 is an element configured to control polarization of the reference light to be inputted to the fiber coupler 38. As the polarized wave controller 36, a configuration such as a paddle type or an inline type used in known ophthalmic devices can be used, thus a detailed description thereof will be omitted.

The fiber coupler 38 is configured to combine the reflected light from the subject eye E and the reference light that were inputted thereto to generate interference light. The fiber coupler 38 is further configured to split the generated interference light into two interference light having phases that differ by 180 degrees from each other, and input them to the balance detector 40. The balance detector 40 is configured to execute a process for differential amplification and a process for reducing noise on the two interference light having the phases that differ by 180 degrees, which were inputted from the fiber coupler 38, to convert them into electric signals (interference signals). The balance detector 40 is configured to output the interference signals to a processor 60.

Here, a configuration of the scanning-alignment optical system 20 will be described with reference to FIG. 2. The scanning-alignment optical system 20 includes a scanning optical system, an anterior-eye-part image capturing system, a fixation target optical system, and an alignment optical system.

Figure 2:
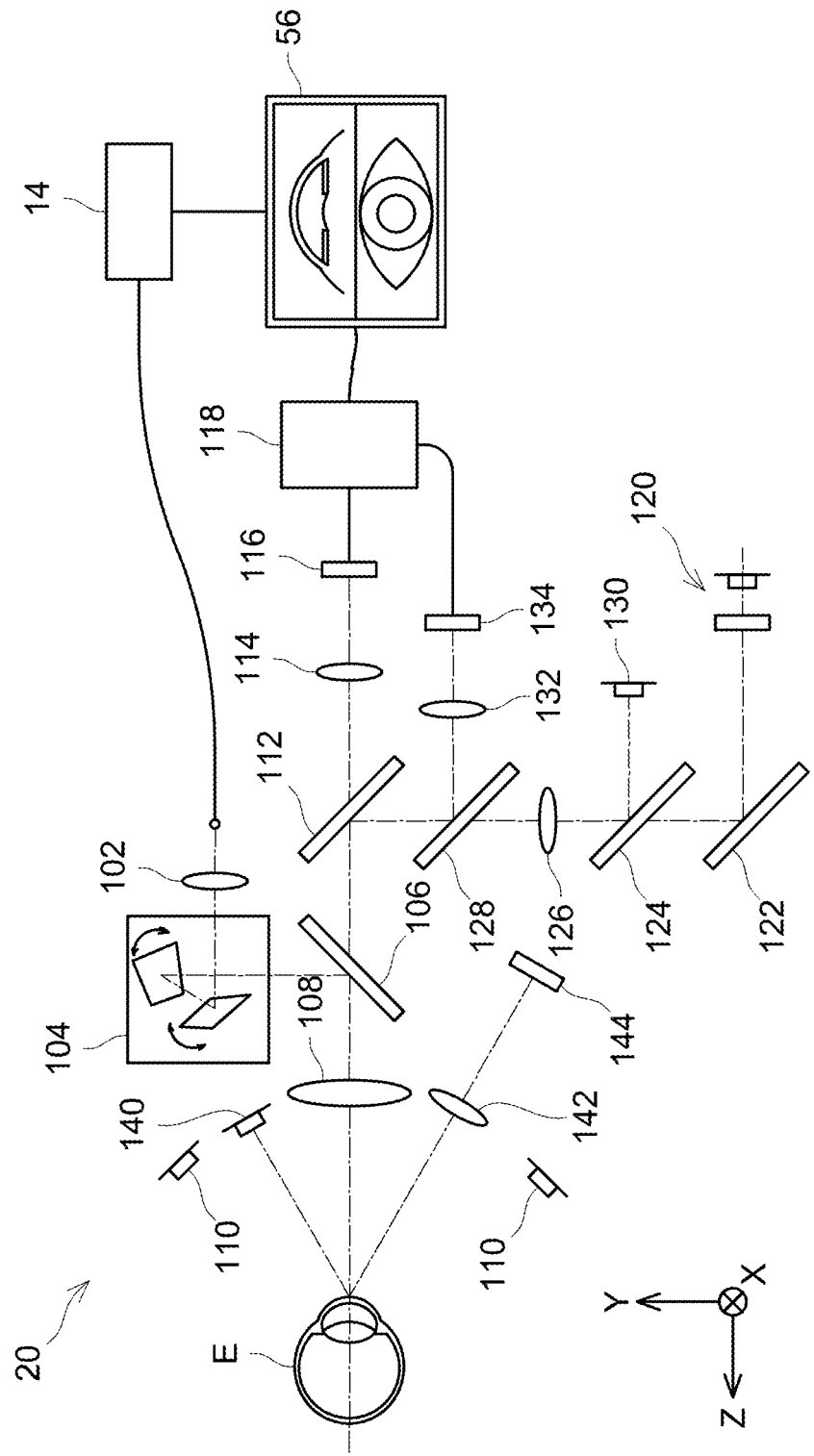
FIG. 2 shows a schematic configuration of a scanning-alignment optical system.

As shown in FIG. 2, the scanning optical system includes a collimator lens 102, a Galvano scanner 104, a hot mirror 106, and an object lens 108. The measurement light outputted from the circulator 18 (see FIG. 1) is emitted to the Galvano scanner 104 through the collimator lens 102. The Galvano scanner 104 is configured to be tilted by a first driver 52 (see FIG. 3), and a position irradiated with the measurement light in the subject eye E is scanned by the first driver 52 tilting the Galvano scanner 104. The hot mirror 106 is irradiated with the measurement light emitted from the Galvano scanner 104 and the measurement light is reflected there at an angle of 90 degrees. The measurement light with which the hot mirror 106 was irradiated is provided to the subject eye E through the object lens 108. Reflected light from the subject eye E is inputted to the circulator 18 after passing through the object lens 108, the hot mirror 106, the Galvano scanner 104, and the collimator lens 102 along a reversed path from the above.

The anterior-eye-part image capturing system includes two illuminating light sources 110, the object lens 108, the hot mirror 106, a cold mirror 112, an imaging lens 114, a CCD camera 116, and an optical controller 118. The two illuminating light sources 110 are configured to irradiate a front side of the subject eye E with illumination light in a visible range. Reflected light from the subject eye E travels through the object lens 108, the hot mirror 106, the cold mirror 112 and the imaging lens 114 and is inputted to the CCD camera 116. Due to this, a front image of the subject eye E is captured. Data of the captured image is subjected to image processing by the optical controller 118 and is displayed on a touch panel 56.

The fixation target optical system includes a fixation target light source 120, cold mirrors 122, 124, a relay lens 126, a half mirror 128, the cold mirror 112, the hot mirror 106, and the object lens 108. Light from the fixation target light source 120 travels through the cold mirrors 122, 124, the relay lens 126 and the half mirror 128, and is reflected on the cold mirror 112. The light reflected on the cold mirror 112 travels through the hot mirror 106 and the object lens 108, and the subject eye E is irradiated with the light. By causing a subject to fix his/her vision at the light from the fixation target light source 120, an eyeball (that is, the subject eye E) can be held still as much as possible.

The alignment optical system is constituted of an XY-direction position detection system and a Z-direction position detection system. The XY-direction position detection system is used to detect positions of the subject eye E (to be more precise, a corneal apex thereof) in XY directions (that is, positional displacements thereof in up-down and right-left directions relative to the ophthalmic device 1). The Z-direction position detection system is used to detect a position of the corneal apex of the subject eye E in a front-rear direction (a Z direction).

The XY-direction position detection system includes an XY-position detection light source 130, the cold mirror 124, the relay lens 126, the half mirror 128, the cold mirror 112, the hot mirror 106, the object lens 108, an imaging lens 132, and a position sensor 134. The XY-position detection light source 130 is configured to emit alignment light for position detection. The alignment light emitted from the XY-position detection light source 130 is reflected on the cold mirror 124, travels through the relay lens 126 and the half mirror 128, and is reflected on the cold mirror 112. The light reflected on the cold mirror 112 travels through the hot mirror 106 and the object lens 108, and the anterior eye part (cornea) of the subject eye E is irradiated with the light.

Since a corneal surface of the subject eye E is spherical, the alignment light is reflected on the corneal surface so as to form a bright spot image on an inner side with respect to the corneal apex of the subject eye E. The reflected light from this corneal surface enters the object lens 108 and is reflected on the cold mirror 112 through the hot mirror 106. The reflected light reflected on the cold mirror 112 is reflected on the half mirror 128 and is inputted to the position sensor 134 through the imaging lens 132. A position of the corneal apex (that is, its position in X and Y directions) is detected by the position sensor 134 detecting a position of the bright spot.

The detection signal of the position sensor 134 is inputted to the processor 60 through the optical controller 118. In this case, alignment is set between the position sensor 134 and the anterior-eye-part image capturing system, and a predetermined (regular) image acquisition position for the corneal apex (a position thereof to be tracked upon acquiring tomographic images) is set. The regular image acquisition position for the corneal apex is, for example, a point that matches a center position of an image captured by the CCD camera 116. The processor 60 is configured to calculate positional displacement amounts of the detected corneal apex (bright point) in the X and Y directions relative to the regular image acquisition position based on the detection of the position sensor 134.

The Z-direction position detection system includes a Z-position detection light source 140, an imaging lens 142, and a line sensor 144. The Z-position detection light source 140 is configured to irradiate the subject eye E with light for detection (slit light or spot light) from an oblique direction with respect to the subject eye E. Reflected light in the oblique direction from the cornea of the subject eye E enters the line sensor 144 through the imaging lens 142. At this occasion, an incident position of the reflected light entering the line sensor 144 varies depending on the position of the subject eye E in the front-rear direction (Z direction) relative to the ophthalmic device 1. Due to this, the position of the subject eye E in the Z direction relative to the ophthalmic device 1 is detected by detecting the incident position of the reflected light. The detection signal of the line sensor 144 is inputted to the processor 60.

The K-clock generator 50 (see FIG. 1) is configured to optically generate sample clock (K-clock) signals from the light of the light source 10 to sample the interference signals at a regular interval frequency (frequency interval that is equalized with respect to light frequency). Further, the generated K-clock signals are outputted toward the processor 60. Due to this, the processor 60 samples the interference signals based on the K-clock signals, by which distortion in the interference signals can be suppressed and deterioration in resolution can be prevented. In the present embodiment, the interference signals that were sampled at timings defined by the K-clock signals are inputted to the processor 60, however, no limitation is placed to this configuration. For example, the processor 60 may execute a process to scale data sampled at a predetermined time interval by using a function indicating a frequency with respect to a preset sweep time, or a sweep profile that is acquired simultaneously therewith. The interference optical system 14 and the K-clock generator 50 are an example of "image capturing unit".

Figure 3:
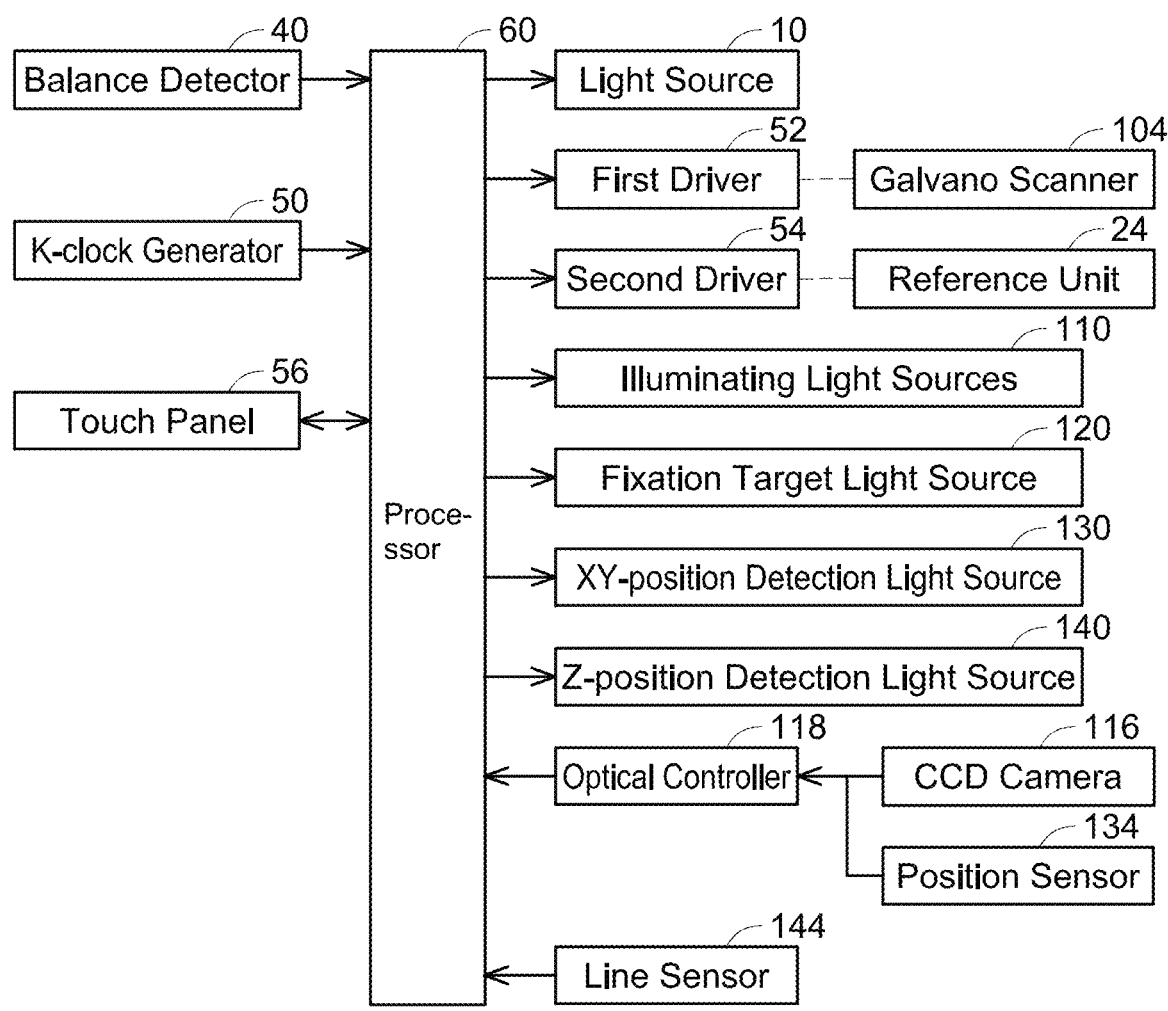
FIG. 3 is a block diagram showing a control system of the ophthalmic device according to the embodiment.

Next, a configuration of a control system of the ophthalmic device 1 according to the present embodiment will be described. As shown in FIG. 3, the ophthalmic device 1 is controlled by the processor 60. The processor 60 is constituted of a microcomputer (microprocessor) constituted of a CPU, a ROM, a RAM, and the like. The processor 60 is connected with the light source 10, the first driver 52, the second driver 54, the illuminating light sources 110, the fixation target light source 120, the XY-position detection light source 130, the Z-position detection light source 140, the optical controller 118, the line sensor 144, the balance detector 40, the K-clock generator 50, and the touch panel 56.

The processor 60 is configured to control on/off of the light source 10 and to drive the Galvano scanner 104 and the reference unit 24 by controlling the first driver 52 and the second driver 54. Further, the interference signals corresponding to intensities of the interference light detected by the balance detector 40 and the K-clock signals generated by the K-clock generator 50 are inputted to the processor 60. The processor 60 is configured to sample the interference signals from the balance detector 40 based on the K-clock signals. Further, the processor 60 executes Fourier transform on the sampled interference signals to specify positions of respective parts (such as the cornea, an anterior chamber, and a crystalline lens) and tissues (such as a nucleus, a cortex, and a capsule of the crystalline lens) of the subject eye E. Data and calculation results inputted to the processor 60 are stored in a memory (not shown).

Further, the processor 60 is configured to control on/off of the illuminating light sources 110, the fixation target light source 120, and the XY-position detection light source 130. The front image of the subject eye E captured by the CCD camera 116 and processed by the optical controller 118 and the position of the corneal apex (bright point) detected by the position sensor 134 via the optical controller 118 are inputted to the processor 60. The processor 60 is configured to calculate the displacement amounts of the corneal apex (bright point) in the XY directions based on the front image of the subject eye E and the position of the corneal apex (bright point) that were inputted. The detection signal of the line sensor 144 is inputted to the processor 60, and the processor 60 is configured to calculate the displacement amount of the subject eye E in the Z direction relative to the ophthalmic device 1. Based on the positional displacement amounts of the corneal apex (bright point) in the X and Y directions detected by the XY-direction position detection system and the positional displacement amount of the subject eye E in the Z direction detected by the Z-direction position detection system, the processor 60 controls a main driver (not shown) such that the aforementioned positional displacement amounts all become 0 and moves a main body of the ophthalmic device 1 relative to a stage (not shown).

Further, the processor 60 is configured to control the touch panel 56. The touch panel 56 is a display device configured to provide various types of information related to measurement results and analysis results of the subject eye E to the examiner and is also a user interface configured to accept instructions and information from the examiner. For example, the touch panel 56 is configured to display images and analysis results of respective tissues of the crystalline lens of the subject eye E that were generated by the processor 60. Further, various settings of the ophthalmic device 1 can be inputted to the touch panel 56 The ophthalmic device 1 of the present embodiment is provided with the touch panel 56, however, no limitation is placed on this configuration. The ophthalmic device 1 simply needs to be able to display and input the aforementioned information, and may be provided with a monitor and an input device (for example, a mouse and a keyboard).

A process of analyzing the crystalline lens of the subject eye E will be described with reference to FIG. 4. Firstly, as shown in FIG. 4, the processor 60 acquires tomographic images of the anterior eye part of the subject eye E (S12). The process of acquiring tomographic images of the anterior eye part of the subject eye E is executed according to the following procedure. Firstly, when the examiner inputs an instruction to start an examination on the touch panel 56, the processor 60 executes alignment between the subject eye E and the ophthalmic device 1. The alignment is executed based on the displacement amounts in the XY directions and the Z direction detected by the alignment optical system. Specifically, the processor 60 moves the main body of the ophthalmic device 1 relative to the stage (not shown) so that the positional displacement amounts of the corneal apex (bright point) in the X and Y directions detected by the XY-direction position detection system and the positional displacement amount of the subject eye E in the Z direction detected by the Z-direction position detection system all become 0.

Figure 5A:
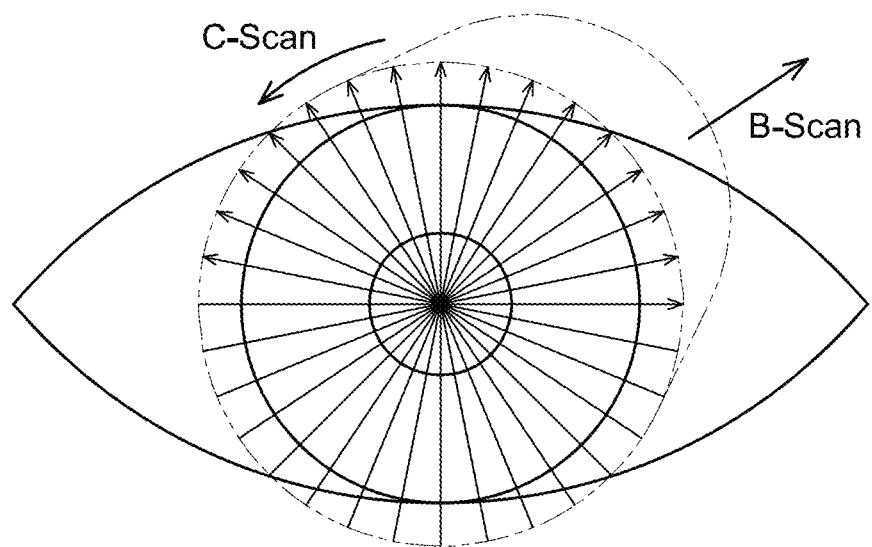
FIGS. 5A and 5B are diagrams for explaining a radial scanning scheme.
Figure 5B:
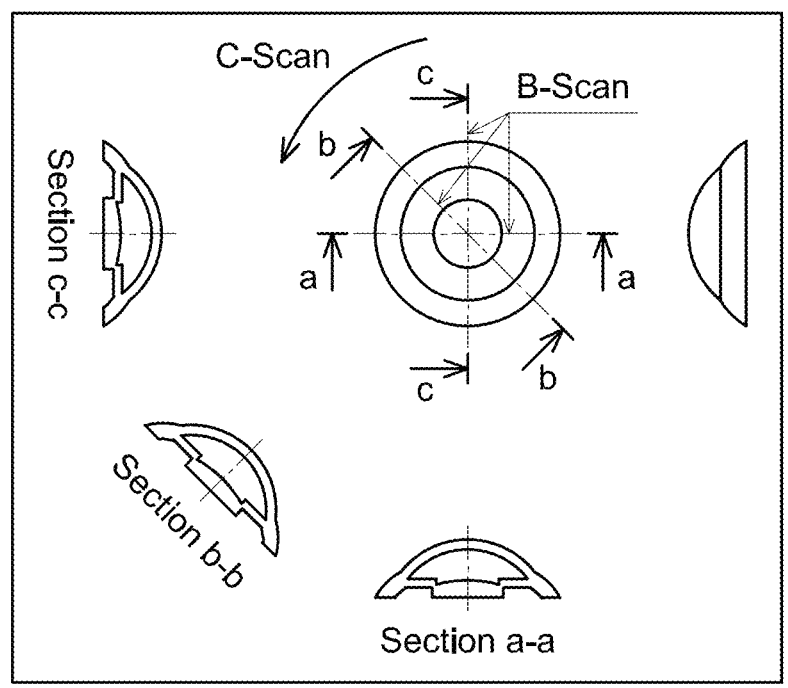
Figure 6A:
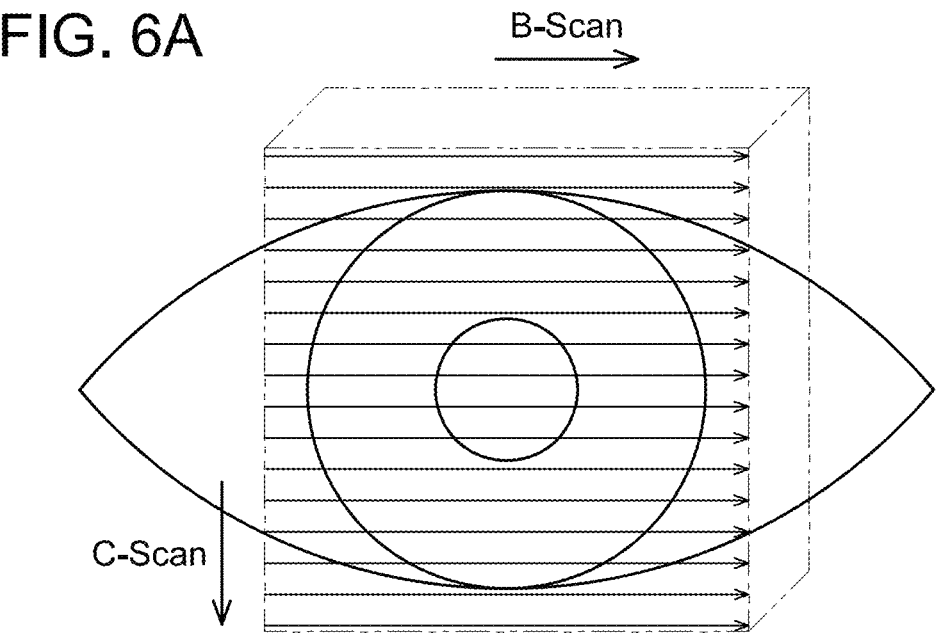
FIGS. 6A and 6B are diagrams for explaining a raster scanning scheme.
Figure 6B:
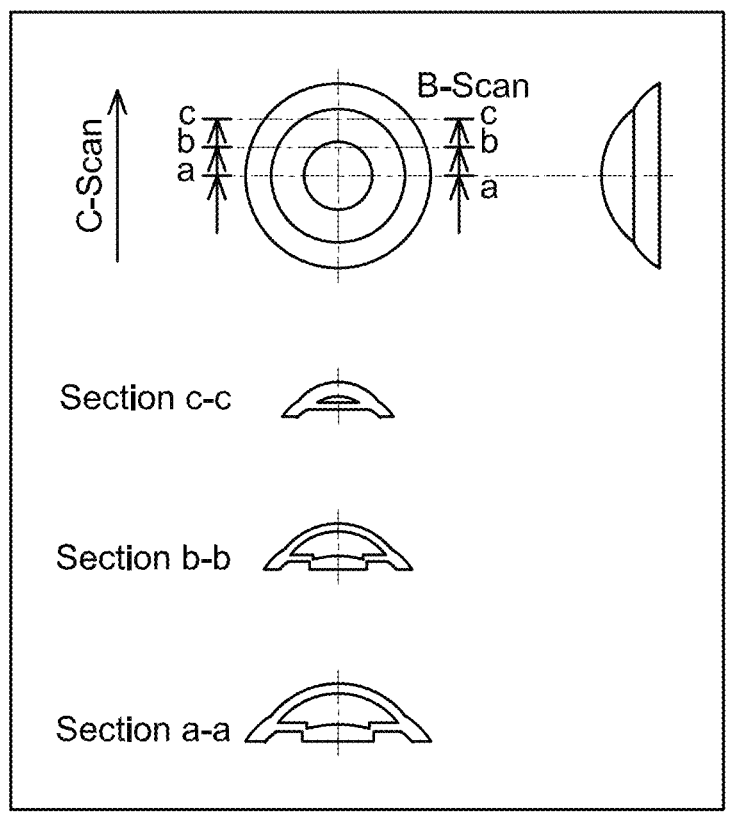

When the alignment is completed, the processor 60 captures tomographic images of the anterior eye part of the subject eye E. In this embodiment, the measurement of the anterior eye part of the subject eye E in step S12 is executed according to a radial scanning scheme. Due to this, the tomographic images of the anterior eye part are acquired over an entire region thereof. That is, as shown in FIG. 5, the tomographic images are captured with B-scan directions set in radial directions from the corneal apex of the subject eye E and a C-scan direction set in a circumferential direction thereof. In this embodiment, the tomographic images are captured in 128 directions radially (specifically, in 128 directions at regular intervals in the circumferential direction) according to the radial scanning scheme. The processor 60 records data of the acquired (captured) tomographic images in the memory. A method of capturing tomographic images of the crystalline lens is not limited to the radial scanning scheme. Any method may be adopted so long as it is able to acquire tomographic images of the crystalline lens over an entire region thereof, and for example, the images may be captured according to a raster scanning scheme. That is, as shown in FIG. 6, the tomographic images may be captured with the B-scan direction in a horizontal direction and the C-scan direction set in a vertical direction relative to the subject eye E.

Figure 7:
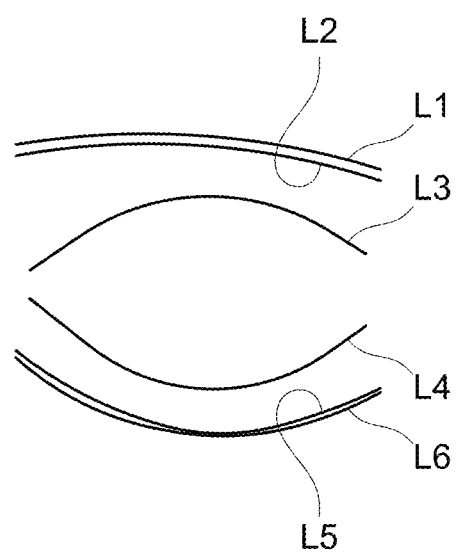
FIG. 7 is a schematic diagram showing a state in which boundaries between tissues in the crystalline lens are detected in a tomographic image.

When the tomographic images of the anterior eye part of the subject eye E are acquired in step S12, the processor 60 detects boundaries between tissues in the crystalline lens based on luminance information included respectively in interference signal information (S14). As shown in FIG. 7, the processor 60 detects, in the crystalline lens, a boundary L1 between an anterior capsule and the anterior chamber (that is, a front surface of the crystalline lens), a boundary L2 between the anterior capsule and the cortex, boundaries L3, L4 between the cortex and the nucleus, a boundary L5 between the cortex and a posterior capsule, and a boundary L6 between the posterior capsule and a vitreous body (that is, a rear surface of the crystalline lens). That is, upon when the measurement light travels through inside of the crystalline lens, a part thereof is reflected at each of the boundaries L1 to L6 between the tissues. The interference signal information includes components of the reflected light that were reflected at these boundaries L1 to L6. In step S14, the boundaries L1 to L6 between the tissues in the crystalline lens are detected based on those signal components included in the interference signal information. In the tomographic images, the cortex is often divided into an anterior chamber side (which is an upper side in FIG. 7) and a vitreous body side (which is a lower side in FIG. 7) by the nucleus. Due to this, hereinbelow, among portions of the cortex divided by the nucleus, a portion of the cortex on the anterior chamber side may be termed "front cortex" and a part thereof on the vitreous body side may be termed "rear cortex". By detecting the boundaries between the tissues in the crystalline lens, the tissues, namely, the anterior capsule (a region between the boundaries L1 and L2), the front cortex (a region between the boundaries L2 and L3), the nucleus (a region between the boundaries L3 and L4), the rear cortex (a region between the boundaries L4 and L5), and the posterior capsule (a region between the boundaries L5 and L6), can be specified.

Next, the processor 60 determines whether or not each of the tissues specified in step S14 includes an abnormality (S16). Whether an abnormality is included or not is determined based on the luminance information of pixels constituting each tissue. For example, different thresholds for the luminance information are preset for the respective tissues, a comparison is performed for each tissue between luminance of each pixel constituting the tissue and the threshold set for the tissue, and a determination that an abnormal portion is present in the tissue is made when the luminance exceeds the threshold. If opacity is present in a tissue, an optic component reflected at the opacified portion is large, which result in high luminance at the opacified portion. The thresholds for the luminance information can be set to include the luminance of the tomographic image including a portion diagnosed as opacified (or a portion suspected as such). In this case, the luminance based on which it is diagnosed that opacity is present differs among the tissues. Due to this, the thresholds are set to different values for the respective tissues. The processor 60 determines, for each of the tissues, whether or not the tissue includes a portion with the luminance higher than the threshold corresponding to the tissue. Then, in a case where the tissue includes the portion with higher luminance than the threshold, the processor 60 determines that an abnormality is present in the tissue. For example, the processor 60 determines that an abnormality is present in the tissue when a number of pixels having higher luminance than the threshold exceeds a set number. In this case, since the tissues differ in size, the set number for executing the abnormality determination may be different among the tissues. In the above example, whether an abnormality is present or not is determined by comparing the luminance of each pixel in the tissue with the threshold, however, no limitation is placed on this method. For example, whether an abnormality is present or not in the tissue may be determined in a simplified manner by comparing an average of the luminance of the pixels constituting the tissue with the threshold.

Next, for each of the tissues in which an abnormality is detected in step S16, the processor 60 creates a two-dimensional image of the tissue (S18). For the anterior capsule, the front cortex, the rear cortex, and the posterior capsule among the aforementioned tissues, the two-dimensional image is created as a front image in which only the tissue is extracted. On the other hand, for the nucleus, the two-dimensional image is created as a tomographic image. In conventional observation methods using a slit lamp microscope, the examiner observes the condition of the nucleus by using a slit lamp. In this case, the examiner observes the nucleus in a similar manner to observing its tomographic image. On the other hand, in the conventional methods, the tissues other than the nucleus (the anterior capsule, the front cortex, the rear cortex, and the posterior capsule) are observed by a retroillumination in which an ocular fundus of the subject eye E is irradiated with illumination light and the observation is performed by reflected light from the ocular fundus. In this case, the examiner observes the tissues other than the nucleus (the anterior capsule, the front cortex, the rear cortex, and the posterior capsule) in a similar manner to observing their front images. As such, by creating a tomographic image for the nucleus as the two-dimensional image and front images for the tissues other than the nucleus (the anterior capsule, the front cortex, the rear cortex, and the posterior capsule) as the two-dimensional images in creating the two-dimensional images for the respective tissues, the examiner can diagnose the tissues similar to the conventional observation methods.

Here, the creation of front image will be described with the front cortex as an example. For example, it is assumed that an abnormality is detected in the front cortex in step S16. That is, it is assumed that a portion having higher luminance than the value set as the threshold for the luminance information of the front cortex is detected in the region specifying the front cortex (the region between the boundaries L2 and L3). In this case, the region specifying the front cortex (the region between the boundaries L2 and L3) is extracted from each of the tomographic images, and the front image constituted only of the front cortex is created. The front image is, for example, an En-face (en-face) image. Specifically, a maximum value and an average value in a depth direction are calculated for each A-scan in three-dimensional data, and the three-dimensional data is compressed to a two-dimensional En-face image.

Figure 8A:
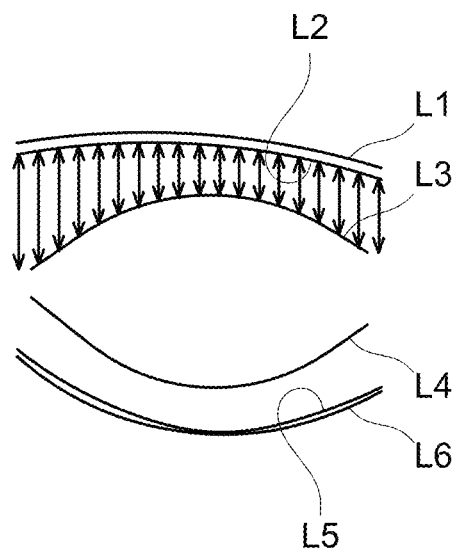
FIGS. 8A and 8B are diagrams for explaining a procedure for creating an En-face image of a front cortex, where
Figure 8B:
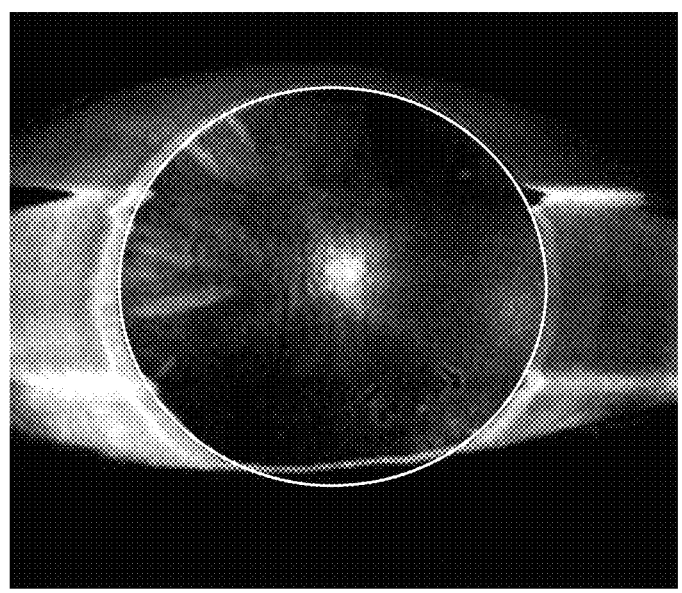

As shown in FIG. 8A, for example, the processor 60 averages, in the region between the boundaries L2 and L3 specifying the front cortex, the luminance in the depth direction shown by arrows for each A-scan. Then, as shown in FIG. 8B, the processor 60 displays the averaged luminance as dots to create the En-face image. For each of the anterior capsule, the rear cortex and the posterior capsule as well, in a case where an abnormality is detected therein in step S16, the processor 60 creates an En-face image that displays only the anterior capsule, the rear cortex or the posterior capsule according to a procedure similar to that for the front cortex. In order to construct an En-face image constituted only of a specific tissue (such as the front cortex), tissues (such as the anterior capsule, the nucleus, the rear cortex, and the posterior capsule) other than the specific tissue (such as the front cortex) are not displayed in the En-face image in overlap. Due to this, the examiner can recognize a condition of the specific tissue easily and accurately.

Next, the creation of two-dimensional tomographic image of the nucleus will be described. In a case where an abnormality is detected in the nucleus in step S16, a tomographic image of the nucleus is colored in plural colors based on the luminance information. The tomographic image used here may have had speckle noise therein removed by executing signal averaging on a tomographic image in a horizontal direction and a plurality of tomographic images adjacent to the aforementioned tomographic image in a circumferential direction (in this embodiment, a total of four tomographic images captured in directions of ±1.4 degrees and ±2.8 degrees with respect to the aforementioned tomographic image). For example, at a portion of the nucleus where opacity is present, the luminance thereof is higher when the luminance in the tomographic image is higher and a degree of the opacity is more severe. In view of this, the luminance information of each pixel is replaced with a hue such that colors change as the luminance increases. For example, green is applied in a case where the luminance is lower than the threshold for the luminance information for detecting an abnormality in the nucleus as used in step S16, and colors are applied such that they gradually change from green to yellow as the luminance increases. Further, colors are applied such that they gradually change from yellow to red as the luminance further increases. For example, in a case where cataract is progressed (for example, in a case of cataract of grade 4 in the classification of WHO), the pixel(s) is replaced with red. By coloring the tomographic image of the nucleus as above, the pixels having the same luminance information in the tomographic image are colored in the same color.

Figure 9:
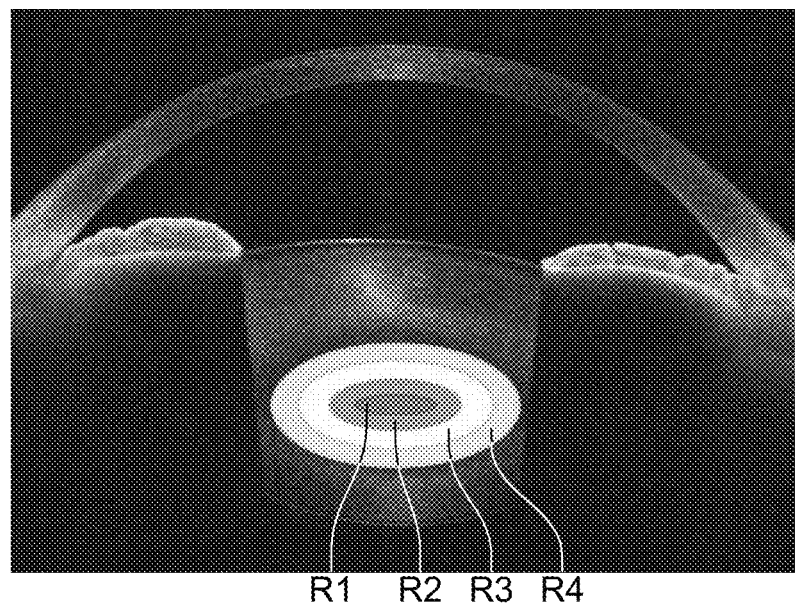
FIG. 9 is a schematic diagram showing a two-dimensional tomographic image of a colored nucleus.

Opacity tends to occur in the nucleus at a central portion thereof rather than at its outer periphery portion in a cross section. Due to this, when the pixels are replaced with the aforementioned hues in the tomographic image of the subject eye E in which cataract is progressed, the central portion of the nucleus is colored in red and other portions thereof are colored such that colors gradually changes closer to green from the central portion toward the outer periphery portion. For example, in the case where cataract is progressed in the nucleus as shown in FIG. 9, a region R1 located at a centermost position in the tomographic image is colored in red, a region R2 adjacent outside the region R1 is colored in orange, a region R3 adjacent outside the region R2 is colored in yellow, and a region R4 located on an outermost side is colored in green.

In the case of the observation using the conventional slit lamp microscopes, the nucleus is observed in different colors depending on progression states of cataract. That is, the nucleus is observed in a color close to white when a degree of progression of cataract is low. Then, as the degree of progression of cataract becomes higher, the color becomes closer to yellow from white, and further becomes close to brown. By coloring the nucleus based on the luminance information as above, the examiner can recognize the condition of the nucleus in colors close to those in the conventional observation methods. In the present embodiment, the luminance information of each pixel is replaced with a hue, however, each pixel may be replaced with a set hue based on an average of the luminance information including the luminance information of its surrounding pixels. Further, in the present embodiment, the pixels are colored by using the hues that change from green to red, however, colors to be used upon replacing the luminance information are not particularly limited. For example, the replacement may use the colors observed by using the conventional slit lamp microscopes (that is, white, yellow, and brown) to convert the tomographic image into an image equivalent to an image observed by using the slit lamp microscopes.

Next, for the tissues in which an abnormality is detected in step S16, grading of the tissues is executed based on the two-dimensional images created in step S18 (S20). For example, for each of the tissues in which an abnormality is detected in step S16, the grading is executed based on the WHO classification.

Specifically, in the case where an abnormality is detected in the cortex (the front cortex and the rear cortex), the cortex is classified based on a ratio (%) of opacity occupying its circumference in the En-face image. Further, opacity at a center of the cortex is classified depending on whether opacity is present within a range of 3 mm from a pupil center or not. For example, in an En-face image 74 (see FIG. 10) of the front cortex, it is assumed that the ratio of opacity occupying the circumference is calculated as 30%. In the WHO classification, if a ratio of opacity occupying a circumference in a cortex is 25% or more and 50% or less, the cortex is classified as grade 2. Further, it is assumed that the opacity is present in the range of 3 mm from the pupil center in the En-face image 74 of the front cortex. In this case, in step S20, the front cortex is classified as grade 2 and further classified as having opacity at the center of the front cortex.

Further, in the case where an abnormality is detected in the nucleus, the nucleus is classified according to a grading method in which determination is made based on comparison with standard photos of the WHO classification. To be more precise, the nucleus is graded based on which of the standard photos of the WHO classification corresponds to the luminance information (that is, the colors applied in step S18) of the nucleus in the tomographic image. For example, in a tomographic image 82 of a colored nucleus (see FIG. 10), it is assumed that the central portion of the nucleus is colored in yellow. If the nucleus is colored in yellow in a tomographic image, the pixels are determined as corresponding to a color of an opacified portion in a standard photo 2 (grade 1) among the standard photos of the WHO classification. In this case, the nucleus is classified as grade 1 in step S20.

Further, in the case where an abnormality is detected in the posterior capsule, the posterior capsule is classified based on a size (mm) of opacity. For example, in an En-face image 78 (see FIG. 10) of the posterior capsule, it is assumed that the size of opacity is calculated as about 4 mm. In the WHO classification, if the size of opacity is 3 mm or more, it is classified as grade 3. Thus, in step S20, the posterior capsule is classified as grade 3.

Finally, results of analyses executed in steps S18 and S20 are outputted to the touch panel 56 (S22). The two-dimensional images 72 to 78 and 82 created in step S18 and the grades of the respective tissues classified in step S20 are displayed on the touch panel 56. That is, for the tissues in which an abnormality is detected, the touch panel 56 displays their two-dimensional images (the En-face images or the colored tomographic image) in which those tissues are displayed, and the grades of those tissues.

Figure 10:
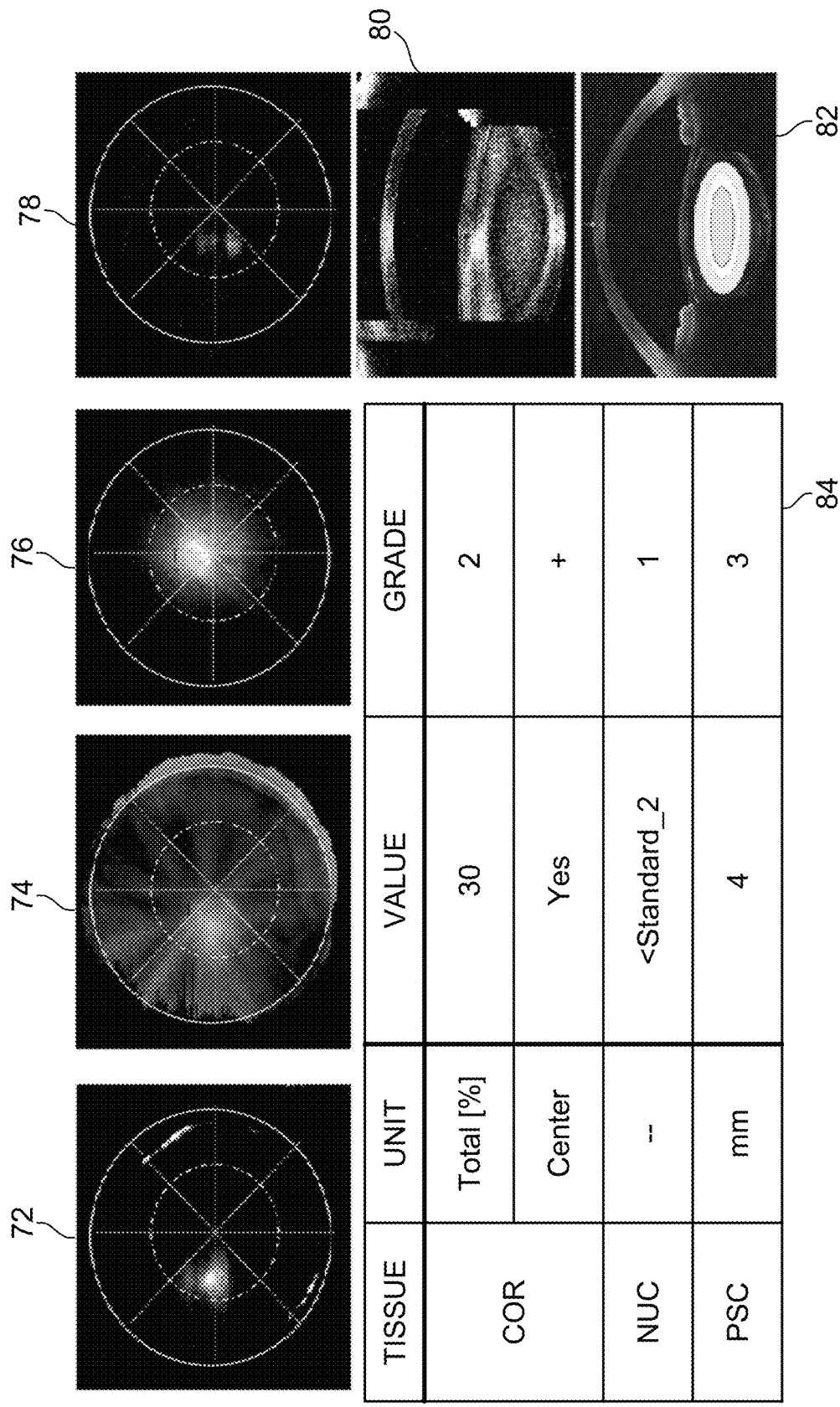
FIG. 10 is a diagram showing an example of analysis results displayed on a touch panel.

For example, FIG. 10 shows an example of the analysis results displayed on the touch panel 56. As shown in FIG. 10, the touch panel 56 displays the En-face image 72 of the anterior capsule, the En-face image 74 of the front cortex, the En-face image 76 of the rear cortex, the En-face image 78 of the posterior capsule, the tomographic image 82 of the colored nucleus, and a table 84 indicating their grading results. Further, the touch panel 56 displays the tomographic image 80 of the crystalline lens. In other words, the touch panel 56 displays the two-dimensional images 72, 74, 76, 78, 82 of the tissues that are created in step S18 due to an abnormality being detected in step S16 and the table 84 indicating the analysis results thereof. The two-dimensional images of the tissues in which an abnormality is detected are displayed on the touch panel 56. Since an abnormality is detected in all the tissues, the two-dimensional images of all the tissues are displayed in FIG. 10, however, two-dimensional image(s) will not be displayed for the tissue(s) in which an abnormality is not detected in step S16. Further, as shown in FIG. 10, the tomographic image 80 acquired in step S12 may be displayed together with the two-dimensional images created in step S18.

The table 84 shows the grading results of the respective tissues. Further, the table 84 indicates respective numerical values calculated for use in the grading determinations. For example, FIG. 10 indicates, in regard to the opacity of the cortex (COR), the value (30) of the ratio (Total (%)) of the opacity calculated in step S20 and presence of the opacity (Yes) at the center thereof (Center). Further, the grades (2 and +) determined based on these values are indicated. Further, in regard to the opacity of the nucleus (NUC), the closest-resembling standard photo (<Standard_2) determined based on the colors applied in step S18 (that is, based on the luminance information) and the grade (1) corresponding to the standard photo are indicated. Further, in regard to the opacity of the posterior capsule (PSC), the value (4) for the size (mm) of the opacity calculated in step S20 and the grade (3) determined based on the value are indicated.

By displaying the two-dimensional images of the tissues in which an abnormality is detected in step S16 and the grades of those tissues on the touch panel 56, the examiner can easily recognize details of the conditions (that is, the images and the grades) of the tissues in which an abnormality is detected.

In the present embodiment, the respective tissues in the crystalline lens of the subject eye E are analyzed based on the tomographic images of the subject eye E captured by using the OCT. Due to this, when the subject eye E is to be captured, a same position of the subject eye E can always be captured, and variations in the analysis results among examinations can be avoided. Due to this, the crystalline lens of the subject eye E can accurately be analyzed. Further, in the conventional methods using the slit lamp microscopes, the slit lamp is used for observing the nucleus, and the retroillumination is used for observing the tissues other than the nucleus. Due to this, in order to observe all the tissues in the crystalline lens, the subject eye E has to be irradiated with the illumination light over a long period of time. In the present embodiment, tomographic images of the respective tissues of the crystalline lens (the anterior capsule, the cortex, the nucleus, and the posterior capsule) can be acquired at once by capturing the tomographic images of the anterior eye part of the subject eye E. Due to this, image-capturing time of the anterior eye part of the subject eye E can be shortened. Further, infrared light is used for the image capture in the OCT, thus the subject does not feel dazzled by the light from the light source during the image capture. Due to this, burden on the subject can be reduced.

Further, in the present embodiment, only for the tissues in which an abnormality is detected in step S16, the creation of two-dimensional images for the tissues in step S18 and the analysis of the tissues in step S20 are executed. Due to this, the processes of steps S18 and S20 can be omitted for the tissues in which no abnormality is detected, and thus processing speed of the processor 60 can be increased.

In the present embodiment, the tissues are graded in step S20 based on the WHO classification, however, a standard classification method used in the grading is not particularly limited. Further, in the present embodiment, the two-dimensional images are created only for the tissues in which an abnormality is detected, however, no limitation is placed on this configuration. Two-dimensional images may be created not only for tissues in which an abnormality is detected but also for tissues in which no abnormality is detected.

Further, in the present embodiment, only the radial scanning scheme is used in capturing the tomographic images of the anterior eye part of the subject eye E in step S12, however, no limitation is placed on this configuration. For example, the radial scanning scheme and the raster scanning scheme may be combined to independently capture tomographic images for creating the two-dimensional tomographic image of the nucleus and tomographic images for creating the front images of the tissues other than the nucleus (the anterior capsule, the front cortex, the rear cortex, and the posterior capsule). Specifically, the anterior eye part of the subject eye E is captured by the radial scanning scheme for creating the two-dimensional tomographic image of the nucleus. For example, tomographic images in 8 directions radially (specifically, in 8 directions at regular intervals in the circumferential direction) are captured. In doing so, scan is executed plural times (for example, 4 times) at a same position in each direction, and the signal averaging is executed. Further, the anterior eye part of the subject eye E is captured by the raster scanning scheme for creating the front images of the tissues other than the nucleus (the anterior capsule, the front cortex, the rear cortex, and the posterior capsule). For example, tomographic images in 256 parallel cross sections are captured.

When the two-dimensional images of the respective tissues are created by using only the tomographic images captured by one scanning scheme (the radial scanning scheme) as in step S12 in the above embodiment, the scan is simply executed only once. Meanwhile, when tomographic images captured by different schemes are used for the two-dimensional image (tomographic image) of the nucleus and the two-dimensional images (front images) of the tissues other than the nucleus, the two-dimensional images can respectively be created with high accuracy. Since the two-dimensional image created for the nucleus is a tomographic image, the radial scan, which captures tomographic images such that each of them includes the corneal apex, is employed. On the other hand, since the two-dimensional images created for the tissues other than the nucleus are En-face images, entireties of the tissues simply needs to be captured. The entireties of the tissues can be captured either with the radial scanning scheme or the raster scanning scheme. However, since a plurality of images is captured upon capturing the tomographic images of the entire anterior eye part of the subject eye E, time is required from a start of the image capture until an end thereof. During the image capture, the subject eye E might move. If the subject eye E moves while being captured according to the radial scanning scheme, displacements might occur between before and after the movement of the subject eye E in the created En-face images. On the other hand, with the raster scanning scheme, such displacements are less likely to occur in the created En-face images even if the subject eye E moves during the image capture. As above, by using the tomographic images captured by schemes suitable for respective tissues in creating the two-dimensional images, the two-dimensional images of the respective tissues can be created highly accurately.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An ophthalmic device comprising:
an image capturing unit configured to capture a tomographic image of a crystalline lens of a subject eye;
a processor; and
a memory storing computer-readable instructions therein, wherein
the computer-readable instructions, when executed by the processor, cause the processor to execute:
detecting a boundary between tissues in a tomographic image of the crystalline lens of the subject eye captured by the image capturing unit, wherein the tissues include a nucleus and a tissue different from the nucleus;

determining whether each of the tissues defined by the boundary includes an abnormality; and for each of at least one of the tissues in which the abnormality is detected, creating a two-dimensional image, the two-dimensional image being a front image of the tissue created by extracting only the tissue in which the abnormality is detected, the front image being an En-face image, and analyzing an analysis item associated with the abnormality based on the created two-dimensional image.

2. The ophthalmic device according to claim 1, further comprising a display unit configured to display an analysis result, wherein when the abnormality is detected, the display unit is configured to display an analysis result of the analysis item.

3. The ophthalmic device according to claim 2, wherein when the abnormality is detected in a nucleus of the crystalline lens, the display unit is configured to display the tomographic image of the crystalline lens captured by the image capturing unit by coloring the nucleus of the crystalline lens in a plurality of different colors based on luminance in the tomographic image of the crystalline lens.

4. The ophthalmic device according to claim 1, wherein for the nucleus, the two-dimensional image is a tomographic image for the nucleus, for the tissue different from the nucleus, the two-dimensional image is a front image of the tissue different from the nucleus.

* * * * *